United States Patent
Cinquin et al.

(10) Patent No.: US 11,931,013 B2
(45) Date of Patent: Mar. 19, 2024

(54) DEVICE FOR TAKING AN INTESTINAL SAMPLE

(71) Applicants: UNIVERSITE GRENOBLE ALPES, Saint Martin d'Heres (FR); CENTRE HOSPITALIER UNIVERSITAIRE GRENOBLE, La Tronche (FR)

(72) Inventors: Philippe Cinquin, Saint Nazaire les Eymes (FR); Denis Favier, La Tronche (FR); Thierry Alonso, St. Ismier (FR); Aziz Bakri, Grenoble (FR); Nawel Khalef, Meylan (FR); Jacques Thelu, Crolles (FR); Sylvain Besson, Villard-Bonnot (FR); Donald Martin, Gieres (FR)

(73) Assignees: UNIVERSITE GRENOBLE ALPES, Saint Martin d'Heres (FR); CENTRE HOSPITALIER UNIVERSITAIRE GRENOBLE, La Tronche (FR)

( * ) Notice: Subject to any disclaimer, the term of this patent is extended or adjusted under 35 U.S.C. 154(b) by 1197 days.

(21) Appl. No.: 16/307,885

(22) PCT Filed: Jun. 7, 2017

(86) PCT No.: PCT/EP2017/063791
§ 371 (c)(1),
(2) Date: Feb. 12, 2019

(87) PCT Pub. No.: WO2017/211872
PCT Pub. Date: Dec. 14, 2017

(65) Prior Publication Data
US 2019/0298318 A1  Oct. 3, 2019

(30) Foreign Application Priority Data
Jun. 7, 2016 (FR) ...................................... 1655187

(51) Int. Cl.
*A61B 10/00* (2006.01)
(52) U.S. Cl.
CPC ...... *A61B 10/0045* (2013.01); *A61B 10/0038* (2013.01); *A61B 2010/0061* (2013.01); *A61B 2562/162* (2013.01)
(58) Field of Classification Search
None
See application file for complete search history.

(56) References Cited

U.S. PATENT DOCUMENTS 4,186,730 A * 2/1980 Bucalo ..................... C12Q 1/24
 435/309.1
4,481,952 A * 11/1984 Pawelec ................. A61B 10/00
 600/593

(Continued)

FOREIGN PATENT DOCUMENTS

| DE | 19801573 A1 | 7/1999 |
| WO | 7900811 | 10/1979 |
| WO | 2005046485 A1 | 5/2005 |

OTHER PUBLICATIONS

International Search Report from corresponding International Application No. PCT/EP2017/063791, dated Jul. 24, 2017, pp. 1-6, European Patent Office, Rijswijk, The Netherlands.

*Primary Examiner* — Alex M Valvis
*Assistant Examiner* — Aurelie H Tu
(74) *Attorney, Agent, or Firm* — HAUPTMAN HAM, LLP

(57) ABSTRACT

A capsule configured for collecting samples in the intestine, comprising a body delimiting at least one compartment for receiving samples and comprising at least one opening for samples intake, and a mobile mechanism for opening and/or closing the opening controlled by the dissolution of a material which is dissolvable in the intestine.

5 Claims, 5 Drawing Sheets

(56) References Cited

U.S. PATENT DOCUMENTS

| | | | |
|---|---|---|---|
| 5,316,015 A * | 5/1994 | Sinaiko | A61B 10/02 |
| | | | 600/593 |
| 5,971,942 A | 10/1999 | Gu et al. | |
| 2003/0065250 A1* | 4/2003 | Chiel | A61B 34/72 |
| | | | 600/115 |
| 2005/0125075 A1* | 6/2005 | Meade | A61F 2/91 |
| | | | 623/23.64 |
| 2007/0161851 A1* | 7/2007 | Takizawa | A61B 34/73 |
| | | | 600/102 |
| 2007/0173738 A1 | 7/2007 | Stoltz | |
| 2016/0038086 A1 | 2/2016 | Wrigglesworth et al. | |

* cited by examiner

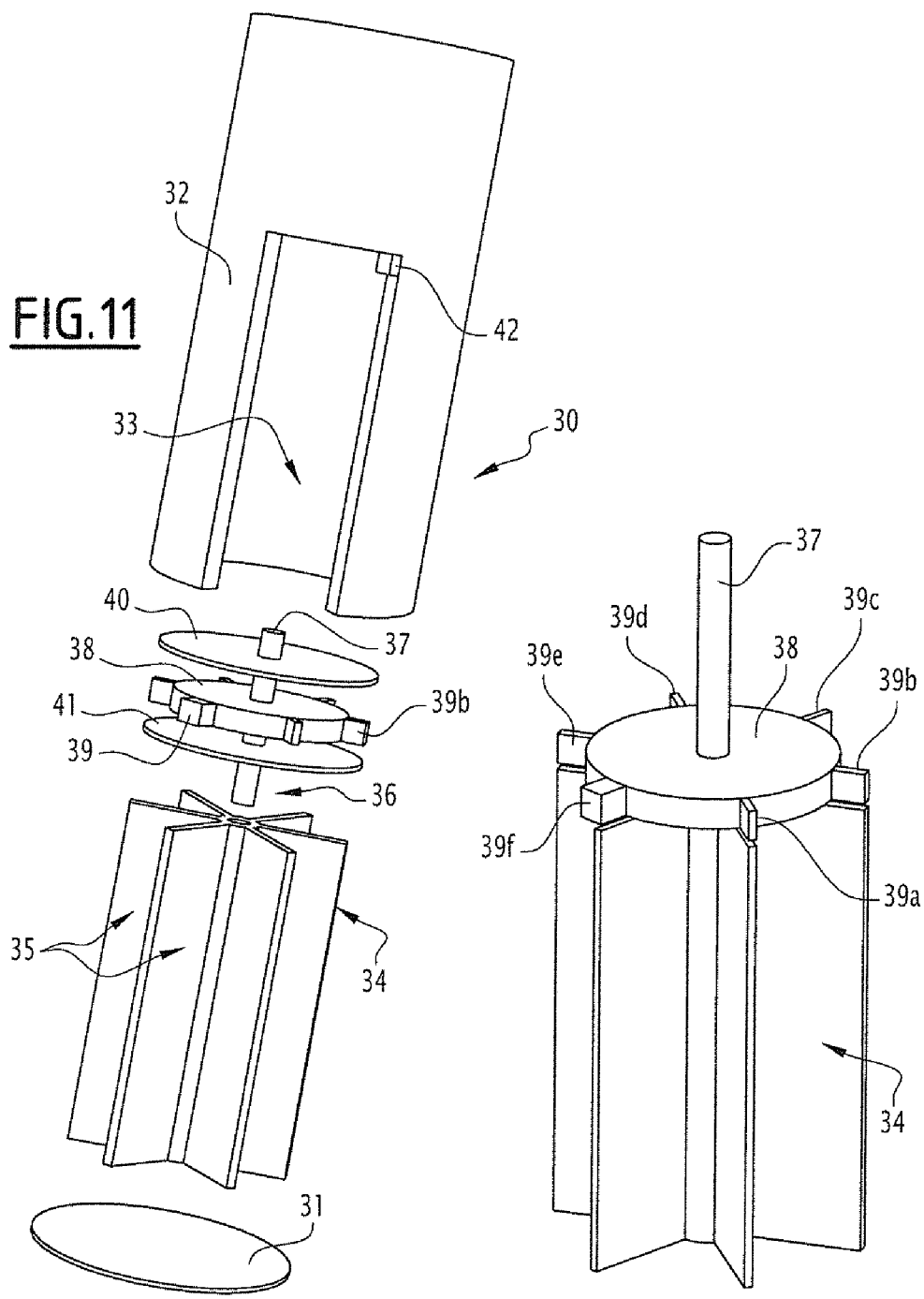

DEVICE FOR TAKING AN INTESTINAL SAMPLE

DOMAIN OF THE INVENTION

The present invention relates to a device making it possible to collect a sample in the intestine, in particular for research and diagnosis purposes.

TECHNOLOGICAL BACKGROUND

At the time when the digestive system and the microbiota thereof is considered as a major subject of interest in human health, in particular in terms of diagnosing pathologies, where new probiotics are continuously developed without actually knowing or being able to know the effects thereof all along the intestine, there is a need for a means making it possible to collect samples representative of determined parts of the tract.

U.S. Pat. No. 5,971,942 describes capsules for collecting samples formed of a casing delimiting an inner volume wherein a low pressure prevails, and equipped with an opening blocked by a seal capable of being dissolved in the intestinal environment, the intestinal liquid thus being suctioned inside the capsule by the pressure difference, and the closing of the capsule being obtained by balancing the pressures outside and inside the capsule. Capsules with several compartments or using several capsules having seals with different dissolution speeds, can be used to collect samples in various places. These capsules do not comprise any mobile opening and/or closing mechanism of the opening controlled by the dissolution of a material that is dissolvable in the intestine. These capsules are limited in inner volume and require a low pressure inside the production.

SUMMARY

The present invention aims to provide a device making it possible to collect samples at different levels in the intestinal tract, and this, preferably in a predetermined manner.

Another aim of the invention is to propose such a device which makes it possible to collect variable volumes, while remaining easily swallowable by the patient.

Another aim of the invention is to propose such a device which has a cost price which is acceptable and easily usable and recoverable.

The invention therefore aims for a capsule configured for the collection of samples in the intestine (small intestine or large intestine). The capsule comprises a body delimiting at least one compartment for receiving samples and at least one opening for samples intake (liquid or intestinal material) associated with an opening and/or closing mechanism controlled by the dissolution of a material which is degradable/dissolvable in the intestine. The entering of a sample through the opening can in particular be done passively through the mechanical opening or by suction by mechanical deployment of the compartment.

The capsule can comprise a material which is dissolvable in the intestine (which means in contact with the content of the intestine), which partially or completely surrounds the body of the capsule and of which the dissolution causes the opening or means that a mechanism causes this opening and/or a suction. The capsule can comprise or house a mobile device for closing the opening which, in the initial state, is immobilised by an obstacle in material which is dissolvable in the intestine, and, after dissolution of this obstacle, is actuated to close the opening.

Notably, devices of the invention have a variation in the outer and inner volume thereof following the dissolution or degradation of a material limiting them initially in a form of reduced volume.

Also, quite notably, devices of the invention comprise several compartments which are linked with the opening successively.

According to a characteristic of the invention, the capsule can be surrounded by a gastro-resistant material, making it possible for the passage, with no obstacle, from the stomach. Once this material dissolves inside the intestine, the capsule can function. The intestinal liquid can dissolve a degradable material, blocking an opening leading to the inside of the compartment, and/or can dissolve a degradable material limiting the body in a folded form, the degradation releasing the body which can be deployed and be opened to the intestinal liquid, and/or dissolve an obstacle or similar in order to release the mobile opening and/or closing device. A person skilled in the art will easily understand that the selection of the material and the dissolution speed thereof in the intestine can be played on, to determine the time when the capsule is ready to function. More than one layer of material can be provided, an outer layer of material to pass the barrier of the stomach, and at least one inner layer to extend the intra-intestinal latency time before the capsule functions.

The invention therefore relates to a capsule configured for collecting samples in the intestine, characterised in that it comprises a body delimiting at least one compartment for receiving samples and comprising at least one opening for samples intake, and a mobile mechanism for opening and/or closing the opening controlled by the dissolution of a material which is dissolvable in the intestine. Preferably, the body of the capsule is totally or partially surrounded a material which is dissolvable (including several materials, as will be explained later, in particular a first gastro-resistant and a material which is dissolvable in the intestine after a determined residence time) in the intestine of which the dissolution triggers or releases the mobile mechanism for opening and/or closing the opening.

In an embodiment, the body of the capsule can be limited in one or more directions in a folded form inside a degradable material in the intestine. Once this material dissolves inside the intestine, the capsule (the body of the capsule) is released and is deployed to take the active form thereof, offering an opening and a compartment volume increased with respect to the non-deployed form. This also has the advantage of having a folded capsule, which is easily swallowable by the individual or to really reduce the volume, that it is possible to swallow several of them at the same time, in particular collected in one same container (gelcap or capsule, which can, at the same time, form the gastro-resistant material). According to a modality, a series of folded capsules can be had, preferably collected in one same larger gelcap or capsule, to which a degradable material in the intestine confers different and predetermined dissolution speeds in the intestine, making it possible to collect samples at different transit times in the intestine. Thus preferably, the capsules have recognition markers, for example a colour or other sign making it possible to class them after collection.

In an embodiment, the capsule is of cylindrical or substantially cylindrical form. Advantageously, conforming with the preceding paragraph, the body thereof can be deployed axially and/or radiated about the cylinder axis.

In a first embodiment, the capsule is of the type of which the body is initially limited in a material which is dissolvable in the intestine, and has a deployed cylindrical form between two rigid discs collected by a spring or a stent avoiding them. The capsule can comprise a sealed and extendable membrane connected to the discs to form the surface of the cylinder. Initially, the membrane extends over a part of the circumference of the cylinder and one of the free edges thereof, preferably reinforced by an extendable or flexible strip (e.g. line) secured to a spring designed to deploy the extendable membrane up to fully closing the cylinder, said spring being initially limited by an obstacle made of material which is dissolvable in the intestine. Preferably, the two discs are equipped, on the section thereof, with a groove each cooperating with a spring connected to the strip, to cause the sealed membrane.

In a second embodiment, the body of the capsule is limited in two orthogonal directions in a folded form inside the material which is dissolvable in the intestine. In a cylindrical form, it is deployed axially and radiated about the axis of the cylinder.

The capsule can comprise, limited in the material which is dissolvable in the intestine, at least one tubular mesh structure, extendable in the two orthogonal directions, in particular of the mesh stent type, possibly made of shape memory or superelastic material, e.g. made of NiTi alloy. Advantageously, this mesh structure is cylindrical. The two bases thereof can be secured to two discs made of extendable material (for example elastomer) to support the radiated extension of the mesh structure. When the capsule is deployed, the two discs avoid one another under the effect of the axial extension of the mesh structure. Each of the discs can be associated with a cylindrical wall made of extendable material extending from the edge of the second disc (or close to the edge of the disc). When the complete deployment of the capsule is achieved and the sample entered into the compartment, the two cylindrical walls come into contact with one another, preferably overlapping at least partially, and close the capsule.

In a first modality, one of the bases of the tubular mesh structure can bear against a first disc made of extendable, solid material. This first disc can be secured to a cylindrical wall made of extendable material extending from the edge of the disc (or close to the edge of the disc), inside the tubular mesh structure over a part of the surface of it. The other base of the tubular mesh structure can bear against a second disc made of extendable material. This second disc can be secured to a cylindrical wall made of extendable material extending from the edge of the second disc (or close to the edge of the disc), inside the tubular mesh structure. This wall is not deployed at rest. It can be associated with a limited deployment spring in non-deployed position by a material which can be dissolved in contact with the content of the intestine and designed to, after dissolution of this material forming an obstacle, deploy the wall associated with the second disc up to overlapping at least partially the wall associated with the first disc.

In a second modality, one of the bases of the tubular mesh structure can bear against a first disc made of extendable material. This first disc can be secured to a cylindrical wall made of extendable material extending from the edge of the disc (or close to the edge of the disc), outside of the tubular mesh structure over a part of the surface of it. The other base of the tubular mesh structure can bear against a second disc made of extendable material. This second disc can be secured to a cylindrical wall made of extendable material extending from the edge of the second disc (or close to the edge of the disc), outside of the tubular mesh structure. A device making it possible to limit the mesh structure axially beyond the deployed rest position thereof can be provided, and size the cylindrical walls such that, in this position, a circumferential opening is cut making it possible for intestinal liquid to enter into the compartment. This device can be connected to the discs by a material which is dissolvable in the intestine, if although once the dissolution is done, the mesh structure takes the deployed rest form thereof closed by the walls. It can relate to an assembly of two bearing springs offset on a disc to which these springs are adhered using an adhesive which can be dissolved with the intestinal liquid, if although after dissolution, the offset bearing means that the springs break free from one another, and the mesh structure takes the deployed rest form thereof, and the cylindrical walls come into contact (preferably, by overlapping at least partially) to close the compartment.

In another embodiment, the body of the capsule houses a blade-shaped structure comprising walls delimiting radiated compartments from a central axis, the structure being secured to a spring, for example, a torsion spring wire, or a mechanical device driving it in rotation. At least one obstacle which can be dissolved in contact with the content of the intestine can be associated with each compartment to not trigger the rotation and the passage of the compartment before the opening that after dissolution of this obstacle. The spring or the mechanical device can exert a constant stress, the rotation being prevented by the presence of a stop against which a dissolvable obstacle bears. When the dissolvable obstacle of a compartment bearing against the stop is dissolved or degraded, the stop is released and the blade-shaped structure rotates by one step until it meets between the stop and the following obstacle, if although said compartment is thus placed before the opening and the sample can enter. Upon the dissolution of the obstacle of the following compartment, the structure rotates by one step and it is the following compartment which is located opposite the opening, and so forth. The set of obstacles can be in contact with the intestinal liquid, the obstacles having predetermined degradation speeds and being reduced from the obstacle associated with the opening of the first compartment and that associated with the last compartment. This can be obtained by selecting the material or by the thickness of the obstacle.

In another embodiment, the body of the capsule is formed of a cage comprising a base structure surrounded by a flexible and elastic sealed membrane, for example made of latex or silicone material, the cage naturally having (at rest, deployed) an ovoid shape between two ends. It can in particular be a cage made of shape memory or superelastic material, e.g. NiTi alloy. The cage is initially limited by a material, in particular one or more material strips, degradable in the intestine, arranged around the sealed membrane, and preferably the non-deployed form is cylindrical. The structure further has an opening at one of the ends thereof or an opening at each of the ends thereof. The dissolution or the degradation of the degradable material strip(s) makes it possible for the structure to be deployed and to suction the intestinal liquid on the inside thereof.

According to a first modality, at an end or two ends, a one-way valve is arranged, making it possible for the suctioning of the liquid into the cage when it is deployed, the valve preventing the exit of the liquid once the cage is filled. Any type of one-way valve can be used comprising a mobile part making it possible for the opening for the liquid to enter when the cage is deployed, and blocking this inlet when the cage is filled. As a simple example, the flexible membrane is returned on itself like an immersion sleeve, towards the inside of the cage, forming a one-way valve. The intestinal liquid is suctioned inside the capsule at the time of the swelling of the cage, it passes the opening freely by avoiding the membrane. Once the capsule is filled, the liquid cannot emerge since the elasticity and the form of the membrane this time constitutes a barrier to the liquid.

According to a second modality, the two openings are associated with a mobile opening and closing mechanism, with a sealing buffer associated with said mobile mechanism to ensure the closing of these openings, only when the structure is deployed. These buffers can advantageously be mounted on a rod extending axially through the structure and openings, and cooperating with bearings placed in these openings. In particular, the mechanism comprises a rod extending axially through the structure, bearings placed in these openings, each bearing having a central orifice with a diameter greater than the diameter of the rod, the sealing buffers being mounted on the rod inside the mesh structure at a place leading them to bear against the bearings when the structure has taken the ovoid shape thereof. The inlet opening is formed by the space left by the rod in the central orifice of the bearings, and the deployment of the mesh structure suctions the sample through this space, until the buffers bear against the bearings.

The body can be formed of a cage comprising a base structure formed of bars surrounded by a flexible and elastic sealed membrane, the cage naturally having (at rest) an ovoid shape. The cage is limited, in particular in cylindrical form by any suitable means, for example one or more material strips which can be dissolved in contact with the intestinal liquid.

In a variant, the cage is made of a shape memory stent type mesh structure, the cage naturally having (deployed at rest) an ovoid shape.

This embodiment is particularly, but not exclusively, suitable for collecting samples of relatively large volume, in particular between around 0.5 mL and around 2 mL.

By degradable or dissolvable material (one word or the other is equally used in the text, except for contrary indication), this means different types of chemical, physico-chemical and/or enzymatic mechanisms.

The material can be fully soluble, or one or more component(s) of the material can be soluble. Thus, the solubility or the degradation/digestion of the material can be obtained by dissolution of a main component such as a polymer or a component such as a binding agent, leading to a total or partial dissolution of the material, sufficient for releasing the capsule from this material. Instead of or in addition, there can also be, an enzymatic mechanism with digestion of a main component such as a polymer (or a mixture of polymers) or a component such as a binding agent, leading to a total or partial digestion of the material, sufficient for releasing the capsule from this material. These materials are capable of undergoing this dissolution or degradation under the physiological conditions of the intestine. As degradable/dissolvable materials in the intestine, synthetic polymers such as PVA (polyvinyl alcohol), poly(acrylic acids) (Carbomer), polyethylene oxides, polymethacrylates, polylactic/glycolic acid (PLGA), etc. can be mentioned. Natural polymers such as polysaccharides: Agarose, Chitosan, Alginates, or proteins such as gelatine or also semi-synthetic such as cellulosic derivatives: Hydroxypropyl methyl cellulose (HPMC), Hydroxide ethyl cellulose (HEC), and Carboxyl methyl cellulose (CMC), gelatine, triglycerides (wax), etc. Different degradation speeds can be obtained as this is known to a person skilled in the art, for example by selecting the material, for example type of material, of polymer, presence or not of additives playing on the solubility of the material, of the polymer or of a component, for example a binding agent, weight composition when there are several components, type of degradation enzymes in the case where the degradation is done enzymatically, and/or the thickness of the material.

As gastro-resistant materials, Cellulose acetophthalate (CAP), Carboxymethyl cellulose (CMC), Hypromellose Acetate Succinate (HPMCAS), Polymethacrylates, Polyvinyl Acetate Phthalate (PVAP), shellac, etc. can be mentioned.

By shape memory alloy or metal, this means a material which has been packaged by the methods known to a person skilled in the art, to take a certain form to 37° C. in the absence of other mechanical stresses exerted on it.

Several small capsules can be collected together in a gelcap or large capsule, as has been stated. It is also possible to arrange a string of several small capsules, connected by cordon or adhered together by a material which does not dissolve in the stomach or in the intestine.

Coloured markers have been mentioned to make it possible for the recognition of recovered capsules. A silicon chip, an RFID chip or similar chip can also be used.

The capsules can also comprise a metal part making it possible to localise them inside the body and/or facilitate the recovery thereof in faeces using a magnet or other magnetic device.

BRIEF INTRODUCTION OF THE DRAWINGS

The invention will now be described in more detail using embodiments taken as non-limiting examples referring to the appended drawings wherein:

FIG. 11 represents an exploded schematic view of a capsule according to a fourth embodiment.

FIG. 12 is a schematic representation raised from the part of the capsule of FIG. 11, delimiting six compartments.

DETAILED DESCRIPTION

Figure 1:
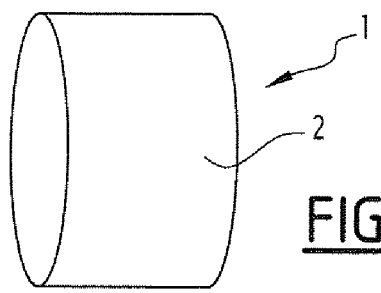
FIG. 1 represents a schematic view of three-quarters of a cylindrical capsule contained in a coating which is dissolvable in the intestine according to a first embodiment.

FIG. 1 represents a schematic view of three-quarters of a capsule 1 contained in a coating 2 which is dissolvable in the intestine according to a first embodiment. The assembly forms a cylinder of which the dimensions will be able to vary, according to different embodiments.

In a first embodiment, the capsule of the type of that represented in FIG. 1 has the following dimensions: from 1 to 6 mm, for example 4 mm in diameter, and from 1 to 6 mm, for example 4 mm in length. Thanks to these reduced dimensions, several, for example 5, 10, 15 or 20, of these capsules can be contained in a large capsule of larger dimensions, for example of length 25 mm and 12 mm in diameter, capable of being taken by the patient orally.

In a second embodiment, the capsule of the type of that represented in FIG. 1 has the following dimensions: 6 to 20 mm, for example 12 mm in diameter, and from 10 to 30 mm, for example 25 mm in length. Thanks to these dimensions, each capsule thus constituted is capable of being taken by the patient orally.

Figure 2:
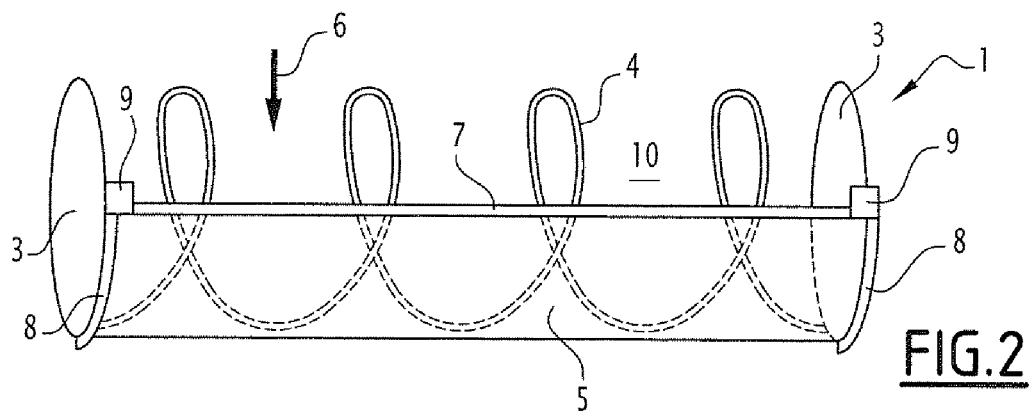
FIGS. 2-4 represent schematic views of the capsule of FIG. 1, deployed after dissolution of the coating, in successive open configurations (FIG. 2), during closing (FIG. 3) and closed (FIG. 4). These views are cross-sectional along a plane containing the (horizontal) axis of the capsule.
Figure 3:
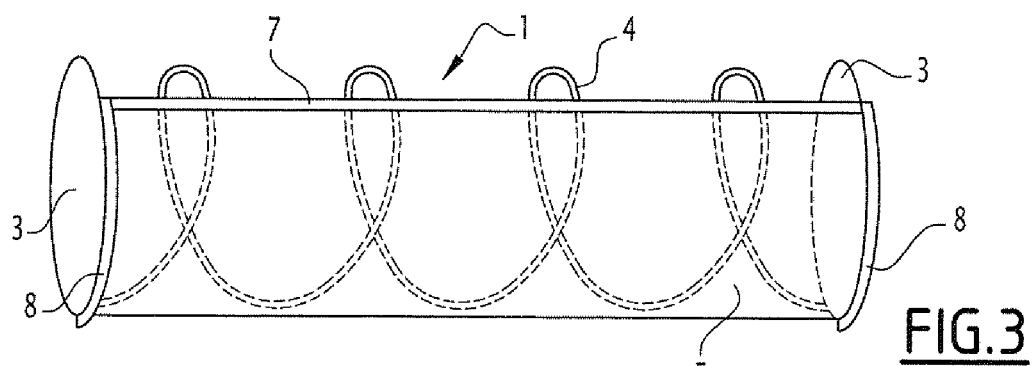
Figure 4:
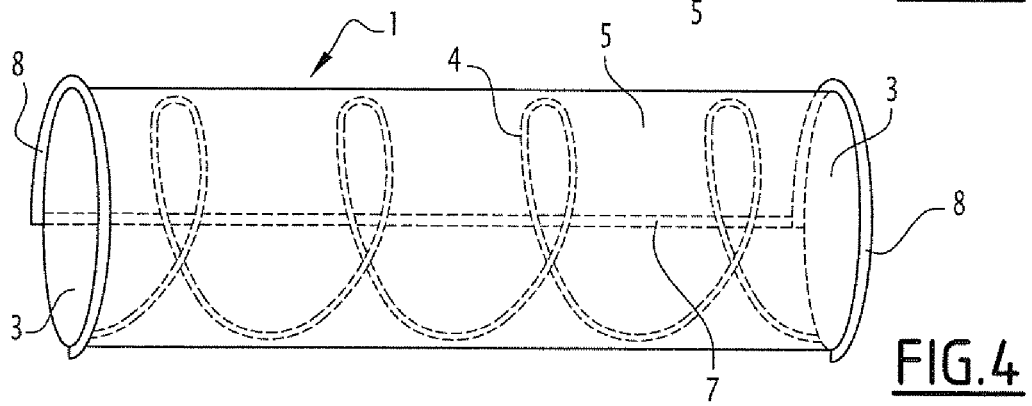

As can be seen in FIGS. 2-4, after dissolution of the coating 2, the capsule 1 is deployed. The capsule 1 has a deployed cylindrical form between two rigid discs 3 combined by a first spring 4 avoiding them, each of the discs having a circular groove (not represented) on the portion thereof. The capsule comprises a sealed and extendable membrane 5 connected to the discs 3 to form the surface of the cylinder. Initially (when the capsule 1 is deployed after dissolution of the coating 2), the membrane 5 extends over a part of the circumference of the cylinder, the free part forming the inlet opening of the sample referenced in the figure by the arrow 6. One of the free edges of the membrane 5 is secured to an extendable line 7 and secured to two cylindrical (helicoidal) springs 8 each arranged in a groove of a disc 3. These springs 8, when they expand after having been released, are designed to drive the line 7 and deploy the extendable membrane 5 progressively and until fully closing the cylinder, the springs 8 driving the line 7 in a rotation movement guided in the grooves of the discs 3. At rest, these springs 8 are compressed and blocked by two obstacles 9 made of material which can be dissolved on contact with the intestinal content, each of the obstacles being arranged at the ends of the line 7 in contact with the discs 3. In FIG. 3, it is seen that the obstacles 9 have disappeared, dissolved on contact with the intestinal liquid, and that the line 7, under the action of the springs 8, has started to close the inner space or compartment 10 of the capsule. In FIG. 4, the movement is stopped and the capsule is closed, the inner compartment being filled with intestinal material (the sample).

The coating 2 is selected for a dissolution in the intestine over a predetermined time, such that collecting the sample is done in the intestinal compartment sought. In particular, it is provided to produce several batches of capsules with specific coatings for each batch, leading to different dissolution speeds. It is then possible to administer to the individual, capsules from these different batches, in order to collect samples at different predetermined places in the intestine.

Advantageously, the capsules from each batch have a particularity (for example, colour of discs) making it possible to identify them.

Figure 5:
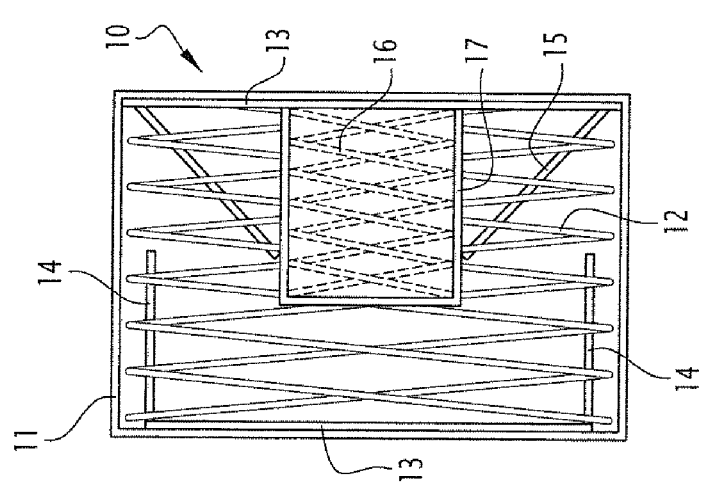
FIG. 5 represents a schematic view of a mesh capsule contained in a coating which is dissolvable in the intestine according to a second embodiment.

FIG. 5 represents a schematic view of a cylindrical mesh capsule 10 contained in a coating 11 which is dissolvable in the intestine, according to a second embodiment. The dimensions can be the same as those described for the embodiment of FIG. 1, for a set of small capsules which could be combined in one larger capsule for oral administration, or for one larger capsule configured to be administered directly. Likewise, these capsules and the coating thereof which are dissolvable in the intestine can be as described for the preceding embodiment, so as to be able to arrange capsules having coatings with different dissolution speeds.

The capsule comprises, contained in the material which is dissolvable in the intestine, a tubular mesh structure which can be extended in the two orthogonal directions (in the axis of the cylinder and radiated). This mesh structure is formed of a stent 12 limited in the two directions (FIG. 5) and deployed (FIGS. 6 and 7), between two discs 13 forming the bases of the cylindrical form of the capsule. One of the discs 13 is secured to a cylindrical wall 14 forming a cylindrical part for delimiting the compartment for receiving samples. The other disc 13 is secured to a second cylindrical wall 15 having, at rest, a truncated cone shape directed towards the centre of the compartment. The discs and walls are made of a flexible, extendable material, for example an elastomer or a compressed material (e.g. pleated), having for example, water-permeable pores and stopping microorganisms, in particular bacteria. The two walls 14 and 15 are situated inside the mesh structure. A second stent 16, smaller than the preceding one, is placed in the compartment to the right of the wall 14, provisionally fixed to this wall by an adhesive being degraded quickly on contact with the intestinal liquid (for example, PVA, Polymethacrylates, amylose, HPMC, etc.). This stent is designed so as to be deployed radiated only. This stent is limited by a degradable material in the intestinal environment.

Figure 7:
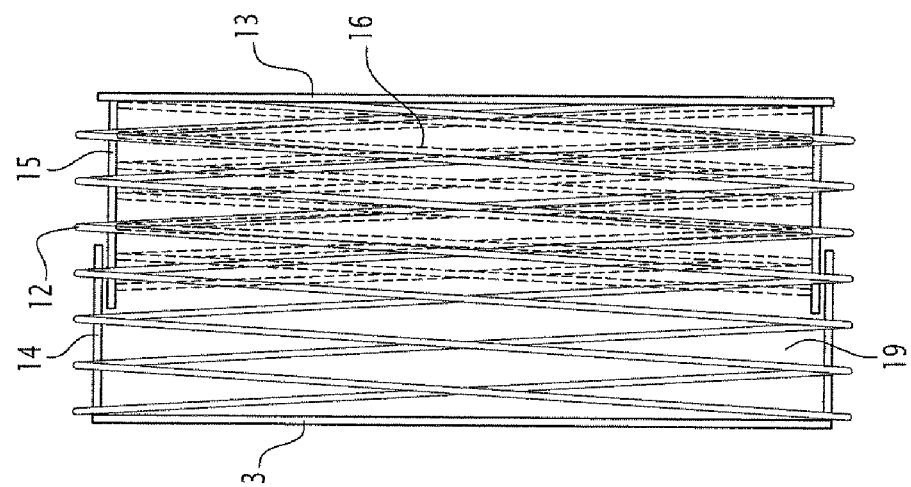
FIGS. 6 and 7 represent schematic views of the capsule of FIG. 5, deployed after dissolution of the coating, in successive open configurations (FIG. 6) and closed (FIG. 7). These views are cross-sectional along a plane containing the (horizontal) axis of the capsule.

During administration to an individual, the capsule is folded as represented in FIG. 5. In the intestine, the material layer 11 will be dissolved leading to the deployment in the two directions of the stent 12, and under the action thereof of the discs 13 and the wall 14. The environment or intestinal liquid can thus enter into the compartment thus outlined by the opening 18. Under the effect of this liquid entering into the compartment, the material layer 17 is itself dissolved, which leads to the radiated deployment of the stent 16 which will be applied to the inner face of the wall 15, pushing it back towards the outside, until it is born against the wall 14 over a superposition zone and closes the compartment 19 (FIG. 7). In addition, a Velcro closing and/or magnetisation to optimise the closing of the compartment 19 can be provided.

Figure 6:
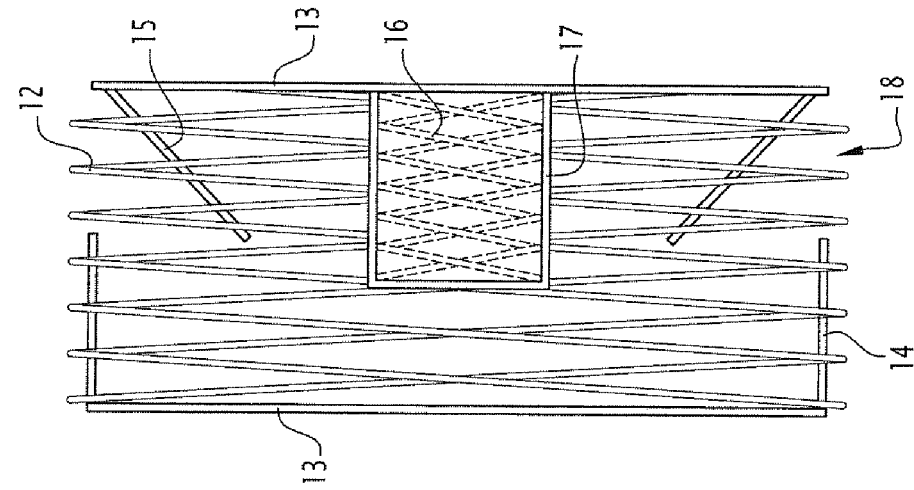

As an example, the length of the capsule is 2 mm and the height thereof (diameter of the cylinder) of 4.5 mm in FIG. 5, then goes to 4 mm in length and 9 mm in height in FIG. 6 and the volume of the compartment is thus 25 μl.

Figure 8:
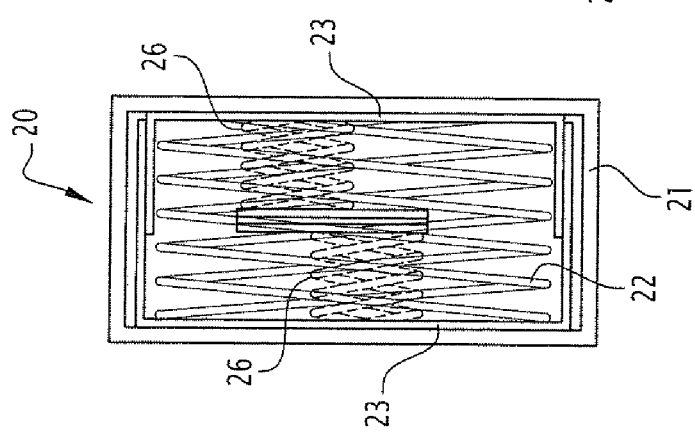
FIG. 8 represents a schematic view of a mesh capsule contained in a coating which is dissolvable in the intestine according to a third embodiment.

FIG. 8 represents a schematic view of a cylindrical mesh capsule 20 limited in a coating 21 which is dissolvable in the intestine, according to a third embodiment. The dimensions can be the same as those described for the embodiment of FIG. 1, for a set of small capsules which could be combined in one larger capsule for oral administration, or for a larger capsule configured to be administered directly. Likewise, these capsules and the coating thereof which are dissolvable in the intestine can be as described for the preceding embodiment, so as to be able to arrange capsules having coatings with different dissolution speeds.

The capsule comprises, contained in the material which is dissolvable in the intestine, a tubular mesh structure which can be extended in the two orthogonal directions (in the axis of the cylinder and radiated). This mesh structure is formed of a stent 22 limited in the two directions (FIG. 8) and deployed (FIGS. 9 and 10), between two discs 23 forming the bases of the cylindrical form of the capsule. The two discs 23 are each secured to a cylindrical wall 24, respectively 25, forming two cylindrical parts for delimiting the compartment for receiving samples. The discs and walls are made of flexible, extendable material, for example an elastomer or a compressed material (e.g. pleated), having for example, water-permeable pores and stopping microorganisms, in particular bacteria. The cylindrical wall carried by the discs are situated outside with respect to the mesh structure. Two springs 26 are placed in the compartment to the right of the discs 23 to which they are fixed provisionally by a polymer which is quickly dissolved by the intestinal liquid (see preceding example), the two springs being fixed together at the centre of the compartment, by way of a disc 27 on either side of which the springs bear offset in opposition, and by an adhesive quickly dissolved by the intestinal liquid. These springs 26 have a greater force to that of the stent 22 in the axial direction, it will be seen that this makes it possible to force them the deploy the stent in the axial direction beyond the rest position of the deployed stent 22.

Figure 9:
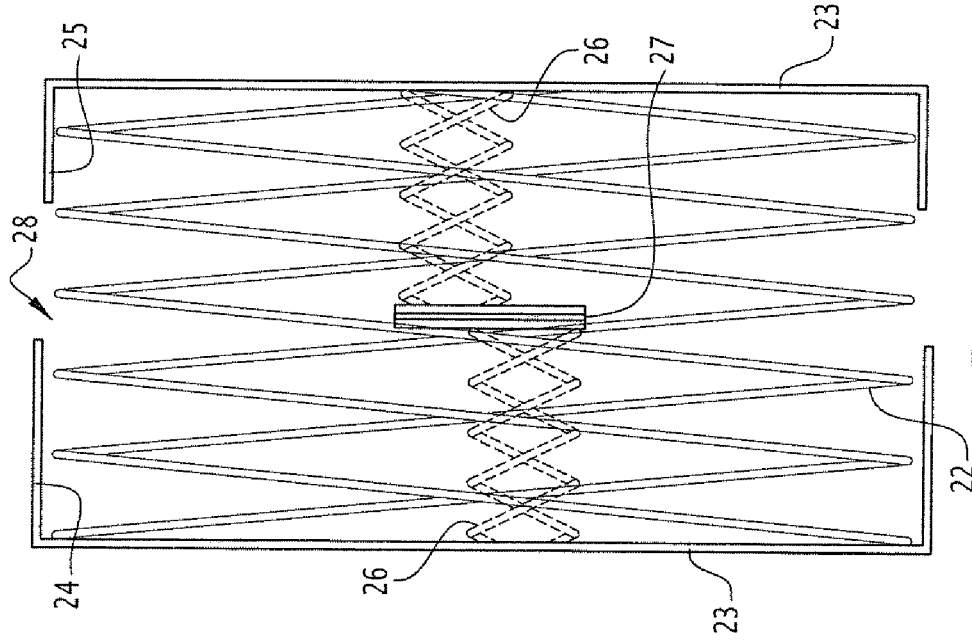
FIGS. 9 and 10 represent schematic views of the capsule of FIG. 8, deployed after dissolution of the coating, in successive open configurations (FIG. 9) and closed (FIG. 10).

During administration to an individual, the capsule is folded as represented in FIG. 8. In the intestine, the material layer 21 will be dissolved leading to the deployment in the two directions of the stent 22, and at the same time, of the discs 23 and of the walls 24 and 25. This also makes it possible for the deployment of the springs 26 in the axial direction, limiting the stent 22 beyond the rest position thereof. The dimensions of the walls 24 and 25 are such that, as long as the springs are deployed, the facing edges thereof are not in contact offering an opening 28 for the entry of the intestinal liquid into the compartment (FIG. 9). Under the effect of this liquid entering into the compartment, the adhesive immobilising the springs 26 is dissolved, releasing the latter, then the bearing offset of the springs on the disc 27 leads the springs to disengage from one another, causing the release thereof at the stent 22, which takes the deployed rest position thereof, leading the walls 24 and 25 to come into contact to close the compartment 29 which thus contains the sample (FIG. 10).

Figure 10:
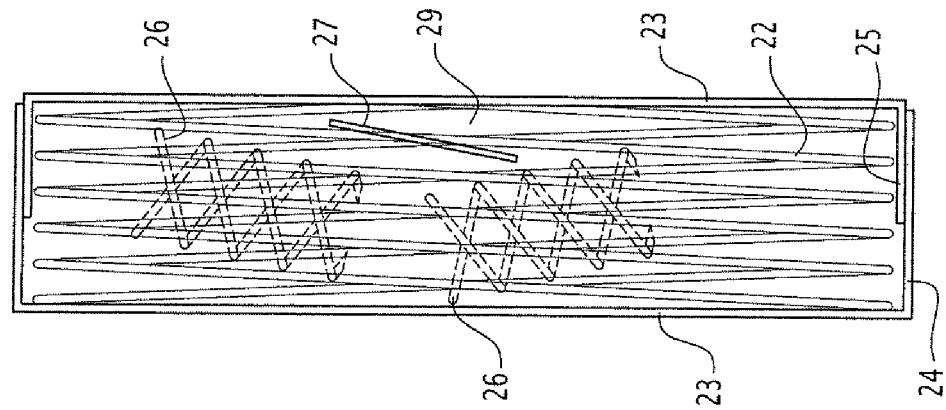

As an example, the length of the capsule is 2 mm and the height thereof (diameter of the cylinder) of 4.5 mm in FIG. 8, then goes to 4 mm in length and 9 mm in height in FIG. 6, and finally to 2 mm in length and 9 mm in height in FIG. 10. Compartment volume: 127 µl.

FIG. 11 represents an exploded, schematic view of a cylindrical capsule according to a fourth embodiment. This capsule 30 comprises, from top to bottom, a base 31, a casing 32 with vertical slot 33, a carousel 34 equipped with several radiated compartments 35 and a central vertical orifice 36, a drive shaft 37 connected to a part 38. Once the assembly is mounted, the slot 33 can be presented successively before the compartments 35 such that the intestinal liquid can be collected, and the drive shaft 37 is coupled with the inside of the central orifice of the carousel 34. FIG. 12 shows a carousel or cylinder with 6 compartments.

Various solutions for driving the carousel in rotation can be considered. A first is a mechanical device for driving the shaft 37 in rotation, for example of clock or kitchen timer, miniaturised.

A second is that the shaft 37 is a torsion wire, or shape memory, which tends to want to go back to the rest position thereof or the initial shape thereof. In this case, this tendency must be stopped, such that the rotation of the carousel and the presentation of a compartment 35 before the slot 33 is controlled and conforms with the process of collecting samples within the intestine.

In the embodiment of FIGS. 11 and 12, the device for driving in rotation is formed of the association of a torsion spring wire 37, a disc 38 carrying, at the periphery thereof, obstacles 39a-39f of increasing dimensions (therefore implying different dissolution times), the disc being surrounded by sealing flanges 40 and 41. The casing 32 carries, at the upper corner of the slot 33 thereof, a fixed stop 42 on which an obstacle abuts, then, when this obstacle is degraded, the torsion spring wire 37 makes the cylinder rotate by one step (by one compartment) until the following obstacle is born against the stop 42.

As an example, a first assembled capsule of 25 mm in height for a diameter of 12 mm, a second of 12 mm in height and 10 mm of diameter. These dimensions can be made to vary within the limits making oral ingestion possible. Then, the number of compartments can be made to vary (for example, from 5 to 20) and at an equal size, the volume of each compartment being reduced as the number increases.

Figure 13:
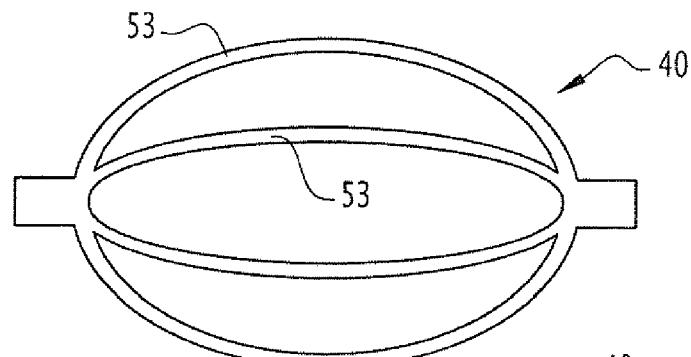
FIG. 13 represents a schematic view raised from a capsule according to a fifth embodiment.
Figure 14:
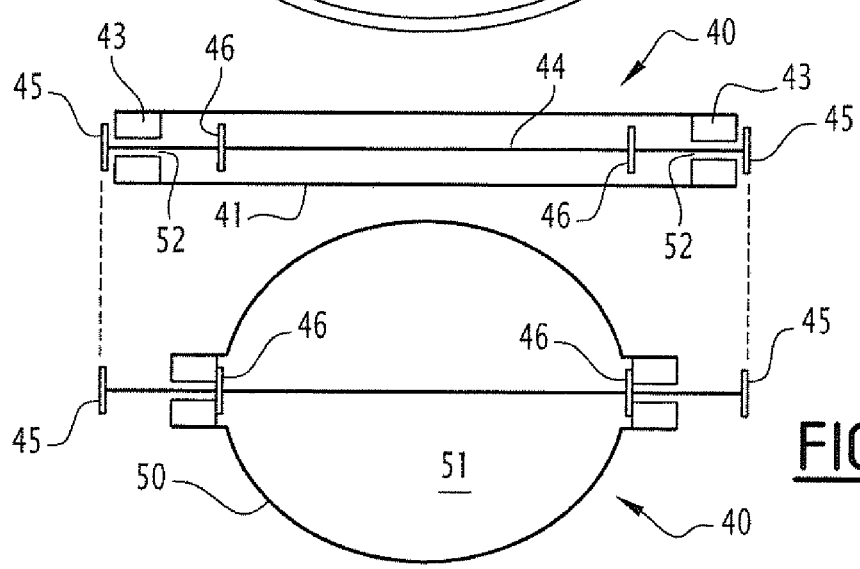
FIG. 14 represents a schematic, cross-sectional view of the capsule of FIG. 13, as a cross section along a plane containing the (horizontal) axis of the capsule, before and after deployment of the capsule and suction of samples, according to a first modality.
Figure 15:
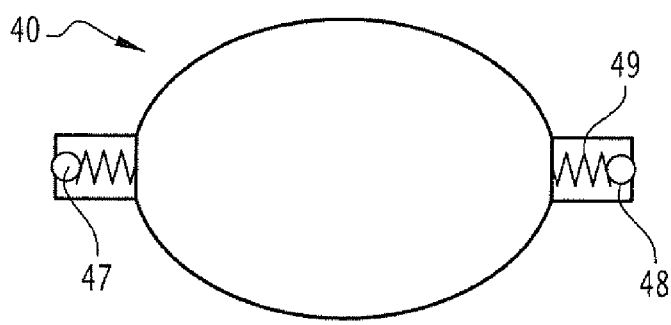
FIG. 15 represents a schematic, cross-sectional view of the capsule of FIG. 13, as a cross section along a plane containing the (horizontal) axis of the capsule, according to a second modality.

FIGS. 13-15 represent a schematic view of a capsule according to a fifth embodiment, functioning with a principle of suctioning the intestinal liquid, but without it being essential to put the inner compartment under low pressure in producing the capsule.

FIG. 14, upper view, shows the capsule 40 in the initial state thereof, such as administered to an individual. This is an NiTi alloy tube 41 cut longitudinally (for example with a laser), except for at the ends where two end parts 42 subsist, and which have undergone a treatment conferring it a shape memory deployed as in FIG. 13 (structures with bars 53). Cylindrical bearings 43 are fixed to the inside of the end parts and a rod 44 extends axially into the tube 41 and the bearings 43. This rod exceeds outside of the tube 41 and is stopped at the two ends thereof by a sealing buffer 45, for example made of elastomer. Two other similar sealing buffers 46 are placed on the rod, inside the tube and in the proximity of the bearings 43. The tube 41 is surrounded by a membrane (schematically represented in FIG. 14, number reference 50), made of flexible silicone material, and resistant to the intestinal environment. Then, one or more strips (not represented) made of material which can be degraded in the intestine, are applied around this membrane, which limits the capsule in the tubular form (FIG. 14, at the top). After dissolution of this/these strip(s), the tube 41 tends to take the deployed form thereof, the buffers 45 no longer thus ensure the sealing at the bearings, the intestinal liquid being suctioned by the light 52 of the bearings forming the inlet opening. When the capsule is fully deployed, the buffers 46 come into contact with the bearings and block the capsule, containing the sample.

FIG. 15 presents a simpler variant, where the end parts of the capsule house the valves 47 of ball valve type with spring 48 and sealing ball 49, only making it possible for intestinal liquid to enter into the compartment 51, during the deployment of it after degradation of the strip(s) made of degradable material.

As an example, the dimensions are selected for a compartment volume of 150 to 300 µl. For example, a cylinder 41 of 6 mm in diameter and of 8 mm in length can be started from, to obtain a suctioned sample volume of around 150 µl in the deployed tube.

Figure 16:
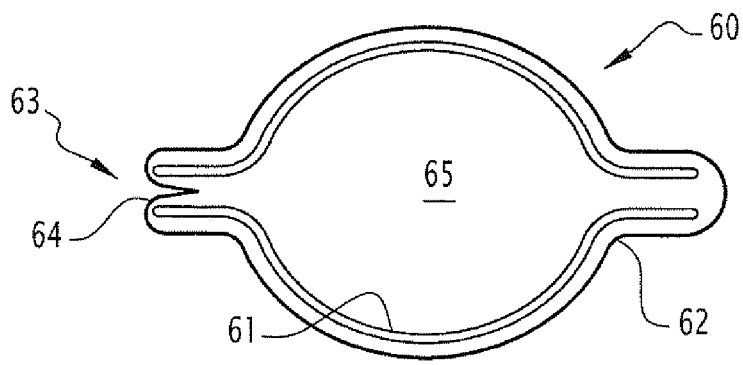
FIG. 16 represents a schematic view raised from a capsule according to a sixth embodiment.

In another embodiment, in FIG. 16, the body of the capsule 60 is formed of a cage 61, for example made of shape memory material, e.g. made of NiTi alloy naturally having (at rest) an ovoid shape. The cage is surrounded by a flexible and elastic membrane 62, for example made of latex or silicone, adjusted to the shape of the cage, at rest. The membrane totally blocks one of the two openings and leaves the other 63 open, as an immersion sleeve covering the cage would do. At the open end, the flexible membrane is returned on itself like an immersion sleeve, and is inserted inside the cage. In this embodiment, the part 64 of the membrane situated inside plays the role of a one-way valve 64. Then, one or more strips (not represented) made of material which can be degraded in the intestine are applied around this membrane, which limits the capsule in a tubular form. After dissolution of this/these strip(s), the cage 60 tends to take the deployed form thereof. The intestinal liquid is suctioned inside 65 of the capsule at the time of the swelling of the cage, it passes the opening freely 63 by avoiding the membrane. Once the capsule is filled, the liquid cannot emerge, since the elasticity and the form of the membrane this time constitutes a barrier to the liquid. The inner pressure of the liquid tends to swell the membrane in 64, which forms rounded structures facing and blocking the opening.

Different degradation speeds can be conferred to the dissolvable materials which can be used in the examples above, and the other possible embodiments of the invention. These controlled degradation speeds can be obtained as this is known to a person skilled in the art, for example, by the selection of the material, for example type of material, of polymer, presence or not of additives playing on the solubility of the material, of the polymer or of a component, for example a binding agent, weight composition when there are several components, type of degradation enzymes in the case where the degradation is done enzymatically, and/or the thickness of the material.

As can be seen, there can already be a layer or outer casing of gastro-resistant material. It can, in particular, be a coating or a capsule wherein the device is inserted.

There can then be one or more layers or one or more obstacles or other dissolvable devices, of which the dissolution will make it possible to open a compartment for collecting samples and/or trigger a sample being collected.

For embodiments using layers or material casings, the following specifications can be applied.

A/ Coating in One Single Layer:

The quality, the quantity, the degree of substituting polymer(s), and the thickness of the layer can make it possible to modulate the duration necessary to activate or release the function. The layer can be composed:

Of a gastro-resistant polymer which is soluble to the pH of the small intestine and wherein other polymers are integrated, excipients which make it possible to modulate the erosion duration of the coating (as indicated in point B below).

Of a polymer which is insoluble in the gastro-intestinal tract (GIT) which is non-erodible (e.g. ethyl cellulose, acrylate and methacrylate, etc.) of which the porosity and thus the diffusion of water is controlled, the expansion of the device, e.g. stent will trigger a breaking of the coating layer.

Of a mixture of polymers which are insoluble and soluble in the GIT (e.g. an ethyl cellulose-Hydroxypropyl methylcellulose HPMC mixture).

B/ Coating in Several Layers:

1—An outer layer:

The following can be used:

A film or a gastro-resistant casing of which the solubility depends on the pH type, for example, cellulose acetophtalate, certain ester methacrylate copolymers, etc., and which only dissolve at basic pH levels.

A membrane which is insoluble in semi-permeable GITs, but which can be broken under the pressure induced by effervescent agents, super-disintegrating agents (Croscarmellose), osmosis (NaCl) or polymers which swell on contact with water (HPMC).

2—Inner layers:

There can be one or more inner layers, composed of one or more polymers, of which the disintegration can be activated and controlled in several manners. The quality of the polymer, number and thickness of the layers can make it possible to modulate the duration necessary to activate the device.

The disintegration of the coating can be done by using:

Polymers which erode by dissolution, by enzymatic digestion, or by any other stimuli such as pH variation.

Hydrophilic polymers such as hydroxypropyl methylcellulose cellulose (HPMC), hydroxyethyl cellulose (HEC) and hydroxypropyl cellulose (HPC) derivatives which swell and erode on contact with water. Controlling the swelling speed makes it possible to control the time necessary such that the water reaches the device and activates the expansion thereof.

The invention claimed is:

1. A capsule configured for collecting samples in the intestine, comprising a body comprising at least one compartment for receiving samples, wherein the body comprises a limited configuration and a deployed configuration, wherein in the limited configuration, the body is totally or paritally surrounded by a material which is dissolvable in the intestine, and the body is limited in two orthogonal directions perpendicular to a central longitudinal axis of the body by the material, the body is deployed to reach the deployed configuration in response to the material being dissolved, the body further comprising at least one opening for sample intake, and a mobile mechanism for opening and closing the at least one opening, the deployment of the body and an actuation of the mobile mechanism being controlled by the dissolution of the material, wherein the body further comprising a device and a flexible and elastic sealed membrane, the device being located inside the flexible and elastic sealed membrane, and the device and the flexible and elastic sealed membrane being two distinct elements, wherein the device is a shape memory cage, the shape memory cage comprising a mesh structure surrounded by the flexible and elastic sealed membrane, and wherein, in the limited configuration, the mesh structure of the shape memory cage is in a cylindrical shape oriented along the central longitudinal axis and, in the deployed configuration, the mesh structure of the shape memory cage is deployed, at least radially along the two orthogonal directions, to form an ovoid shape, in order to deploy the flexible and elastic sealed membrane and give to the body an ovoid shape.

2. The capsule according to claim 1, wherein the body is totally or partially surrounded by a material which is dissolvable in the intestine, and wherein the dissolution of the material triggers or releases the mobile mechanism for opening and closing the at least one opening.

3. The capsule according to claim 1, wherein the shape memory cage is limited by the material which is dissolvable in the intestine, the mesh structure further haviing an opening at each of two ends thereof respectively, and for each opening, a sealing buffer associated with the mobile mechanism to ensure the closing of the openings of the two ends, only when the mesh structure is in the deployed configuration, wherein the closing of the opening is achieved by the movement of the sealing buffer or a sealing ball.

4. The capsule according to claim 3, wherein the mechanism comprises a rod extending axially through the mesh structure, bearings placed in the opening at each of the two ends, each bearing having a central orifice of diameter greater than the diameter of the rod, the sealing buffer being mounted on the rod at a place bringing them to bear against the bearings when the structure has taken the ovoid shape thereof.

5. The capsule according to claim 1, wherein the shape memory cage is limited by a material which is dissolvable in the intestine, the mesh structure further having at least one opening at an end and a one-way valve is placed in the at least one opening.

* * * * *